(12) United States Patent
Mahaney et al.

(10) Patent No.: US 7,612,210 B2
(45) Date of Patent: Nov. 3, 2009

(54) PROCESS FOR SELECTIVE SYNTHESIS OF ENANTIOMERS OF SUBSTITUTED 1-(2-AMINO-1-PHENYL-ETHYL)-CYCLOHEXANOLS

(75) Inventors: Paige Erin Mahaney, Pottstown, PA (US); Madelene Miyoko Antane, West Windsor, NJ (US); Jerry Shunneng Sun, Blauvelt, NY (US)

(73) Assignee: Wyeth, Madison, NJ (US)

( * ) Notice: Subject to any disclaimer, the term of this patent is extended or adjusted under 35 U.S.C. 154(b) by 367 days.

(21) Appl. No.: 11/633,207

(22) Filed: Dec. 4, 2006

(65) Prior Publication Data

US 2007/0135449 A1 Jun. 14, 2007

Related U.S. Application Data

(60) Provisional application No. 60/742,560, filed on Dec. 5, 2005.

(51) Int. Cl.
*C07D 263/04* (2006.01)
(52) U.S. Cl. .................. 548/230; 548/215; 548/225; 548/229
(58) Field of Classification Search .......... 548/215, 548/225, 229, 230, 236
See application file for complete search history.

(56) References Cited

U.S. PATENT DOCUMENTS

| | | | |
|---|---|---|---|
| 4,535,186 A | 8/1985 | Husbands et al. | |
| 4,761,501 A | 8/1988 | Husbands et al. | |
| 5,506,270 A | 4/1996 | Upton et al. | |
| 5,530,013 A | 6/1996 | Husbands et al. | |
| 6,689,912 B2 | 2/2004 | Weber et al. | |
| 6,717,015 B2 * | 4/2004 | Keltjens et al. | 564/355 |
| 7,026,508 B2 | 4/2006 | Winkley et al. | |
| 2007/0014859 A1 | 1/2007 | Shah et al. | |
| 2007/0015791 A1 | 1/2007 | Shah et al. | |
| 2007/0015824 A1 | 1/2007 | Shah et al. | |
| 2007/0015828 A1 | 1/2007 | Shah et al. | |

FOREIGN PATENT DOCUMENTS

| | | |
|---|---|---|
| EP | 0 639 374 A2 | 2/1995 |
| EP | 0 654 264 A1 | 5/1995 |
| WO | WO 2005/037809 A1 | 4/2005 |
| WO | WO 2007/011594 A2 | 1/2007 |
| WO | WO 2007/011619 A2 | 1/2007 |

OTHER PUBLICATIONS

[Patani, George A. Bioisosterism: A rational Approach in Drug Design. Chem. Rev. 96 (1996) 3147-3176.]*
[Treves, Gino R. Basic Esters and Quaternary Derivatives of β-Hydroxy Acids as Antipasmodics. Journal of the American Chemical Society, 74(1) (1952) 46-48.]*
Testa, Prodrugs Revisited: The "Ad Hoc" Approach as a Complement to Ligand Design, Medicinal Research Reviews, vol. 16, No. 3,pp. 233-241, (May 1996).
Brooks et al, Boron Trichloride/Tetra-n-Butylammonium Iodide: A Mild, Selective Combination Reagent for the Cleavage of Primary Alkyl Aryl Ethers, J. Org. Chem., 64, pp. 9719-9721, (1999).
Pento, J.T., Drugs of the Future, vol. 13, Issue 9, pp. 839-840, (1988).
Takacs et al, Preparation of Chiral Oxazolidin-2-Ones and Vicinal Amino Alcohols, J. Org. Chem. 63, pp. 2742-2748, (1998).
Yardley et al, 2-Phenyl-2-(1-Hydroxycycloalkyl)Ethylamine Derivatives: Synthesis and Antidepressant Activity, J. Med. Chem., 33, pp. 2899-2905, (1990).

* cited by examiner

*Primary Examiner*—Kamal A Saeed
*Assistant Examiner*—Samantha L Shterengarts
(74) *Attorney, Agent, or Firm*—Doina G. Ene; David R. Kurlandsky; A. David Joran

(57) ABSTRACT

A process for the enantioselective synthesis of an (S)- or (R)-1-[2-dimethylamino)-1-(methoxyphenyl)ethyl]cyclohexanol and analogues or salt thereof are described. The method involves the steps of (a) reacting an (S) or (R) 4-benzyloxazolidinone with a mixed anhydride of a methyoxyphenylacetic acid under conditions which form a oxazolidinone, (4S)- or (4R)-4-benzyl-3-[methyoxyphenyl]acetyl]-oxazolidin-2-one, (b) treating the (4S)- or (4R)-4-benzyl-3-[(methoxyphenyl)acetyl]-1,3-oxazolidin-2-one with an aprotic amine base and titanium chloride in a chlorinated solvent under conditions which permit formation of the corresponding anion, (c) mixing the corresponding anion with titanium chloride and cylcohexanone under conditions which permit an aldol reaction to form the corresponding (4S)- or (4R)-4-benzyl-3-[(2R)-2-(1-hydroxycyclohexyl)-2-(methoxyphenyl)acetyl]-1,3-oxazolidin-2-one,(d) hydrolyzing the (4S)— or (4R)-4-benzyl-3-[(2R)-2-(1-hydroxycyclohexyl)-2-(methoxyphenyl)acetyl]-1,3-oxazolidin-2-one to form a chiral acid (2S or 2R)-(1-hydroxycyclohexyl)-methoxyphenyl)acetic acid, (e) coupling the chiral phenylacid to a secondary amine to form an amide, and (f) reducing the amide to form an (S) or (R) 1[2-dimethylamino)-1-(methoxyphenyl) ethyl]cyclohexanol or a salt thereof.

13 Claims, No Drawings

PROCESS FOR SELECTIVE SYNTHESIS OF ENANTIOMERS OF SUBSTITUTED 1-(2-AMINO-1-PHENYL-ETHYL)-CYCLOHEXANOLS

CROSS-REFERENCE TO RELATED APPLICATIONS

This application claims the benefit under 35 USC 119(e) of US Provisional Patent Application No. 60/742,560, filed Dec. 5, 2005.

BACKGROUND OF THE INVENTION

Venlafaxine, (±) 1-[2-(dimethylamino)-1-(4-methoxyphenyl)ethyl]-cyclohexanol, is a nontricyclic compound which has been described for use in treatment of depression, general anxiety disorders, and vasomotor symptoms.

Venlafaxine and the acid addition salts thereof are described in U.S. Pat. No. 4,535,186. These compounds have been studied extensively and described in, for example, U.S. Pat. No. 4,761,501 and Pento, J. T. *Drugs of the Future* 13(9):839-840 (1988).

The hydrochloride salt of venlafaxine is currently commercially available in the United States under the trade name Effexor®. Effexor®, which is a racemic mixture of the (+) and (−) enantiomers of venlafaxine, is indicated for the treatment of depression. This drug is typically administered orally to adults in compressed tablet form taken two or three times a day within the range 75 to 350 mg/day.

EP 0639374 describes the use of venlafaxine in the treatment of obesity, panic disorder, post-traumatic stress disorder, late luteal phase dysphoric disorder, attention deficit disorder, Gilles de la Tourette syndrome, bulimia nervosa, generalized anxiety disorder or Shy Drager syndrome. EP-A-654264 teaches the use of venlafaxine in treating incontinence. U.S. Pat. No. 5,506,270 (Upton et al.) claims venlafaxine's use in methods of treating hypothalamic amenorrhea in non-depressed women. U.S. Pat. No. 5,530,013 (Husbands et al.) claims venlafaxine's use for enhancing cognition.

Vasomotor symptoms (VMS), referred to as hot flushes and night sweats, are the most common symptoms associated with menopause, occurring in 60% to 80% of all women following natural or surgically-induced menopause. Such symptoms have also been described in patients undergoing chemotherapy, e.g. for breast cancer. Venlafaxine has been described for the treatment of VMS in e.g. US Published Patent Application No. 2005 01435979, and the documents cited therein.

Syntheses of venlafaxine and other 2-phenyl-2-(1-hydroxycycloalkyl)ethylamine analogs have been described, for example, in JP Yardley, et al., *J Med Chem*, 1990, 33, 2899-2905.

Additional useful 2-phenyl-2-(1-hydroxycycloalkyl)ethylamines have been described, for example, in US20050143394.

What are needed are alternative methods and intermediates useful for the synthesis of venlafaxine compounds.

SUMMARY OF THE INVENTION

The present invention provides a process for selectively synthesizing the desired enantiomer of an intermediate useful in the production of a 2-phenyl-2-(1-hydroxycycloalkyl) ethylamines of formula I:

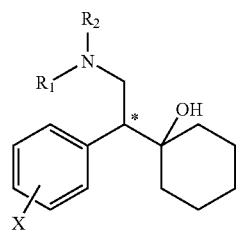

Wherein X is $OCH_3$ or $CF_3$, $R_1$ and $R_2$ are each independently selected from $C_1$-$C_3$ alkyl, or together with the nitrogen they are attached form a 1,4-piperazine ring wherein said piperazine ring is substituted with from 0 to 2 methyl groups.

In one embodiment, the process of the invention comprises the steps of:

treating a (4S or 4R)-4-benzyl-3-[(methoxyphenyl) acetyl]-1,3-oxazolidin-2-one having the structure

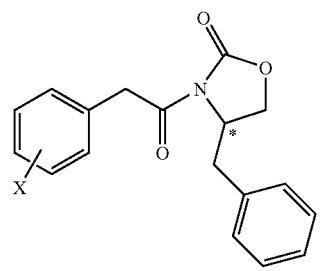

wherein X is selected from the group consisting of methoxy or trifluoromethoxy;
with a base under conditions which permit formation of the corresponding anion; and
mixing the corresponding anion with cyclohexanone under conditions which permit an aldol reaction to form the corresponding (4S or 4R)-4-benzyl-3-[(2R or 2S)-2-(1-hydroxycyclohexyl)-(methoxyphenyl)acetyl]-1,3-oxazolidin-2-one.

In some embodiments the base is an aprotic amine.
In some embodiments, the anion is formed in a solvent, said solvent comprising at least one chlorinated hydrocarbon.
In some embodiments, the reaction between the anion and cyclohexanone is carried out in the presence of a Lewis acid.
In some embodiments, the reaction between the anion and cyclohexanone is carried out in the presence of $TiCl_4$.

In another aspect the invention provides a 4-benzyl-3-[2-(1-hydroxycyclohexyl)-2-(3-trifluoromethoxyphenyl) acetyl]-1,3-oxazolidin-2-one, wherein said compound has the structure

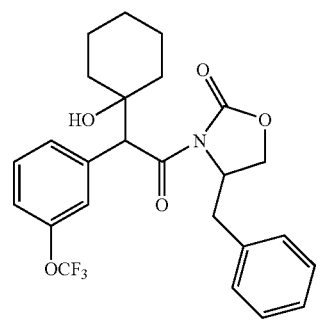

In some embodiments, this invention provides essentially a single diastereomer of 4-benzyl-3-[2-(1-hydroxycyclohexyl)-2-(3-trifluoromethoxyphenyl)acetyl]-1,3-oxazolidin-2-one, wherein said diastereomer is

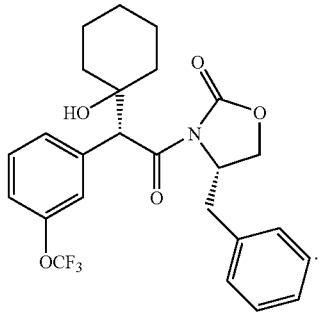

In another embodiment, this invention provides a compound having the structure:

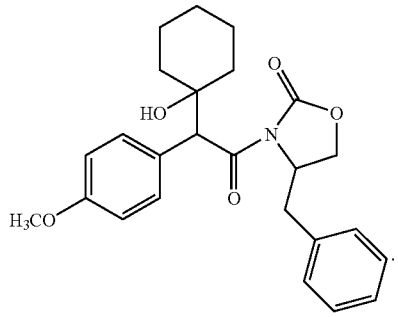

In some embodiments, this invention provides essentially a single diastereomer, wherein said diastereomer is

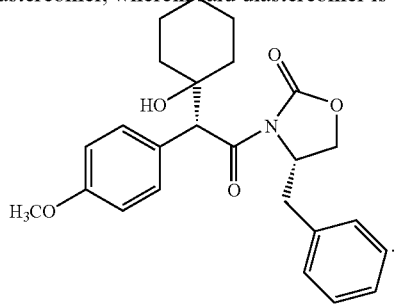

In certain embodiments, this invention provides a compound of formula

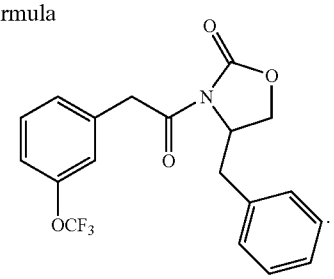

In some embodiments, this invention provides essentially a single enantiomer, wherein said enantiomer is

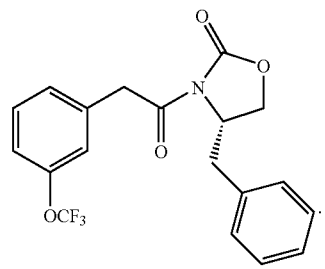

In a further aspect, the invention provides a process for the selective synthesis of an enantiomer of a compound of formula I or a derivative or salt thereof. This method comprises the steps of:

(a) reacting an (S)- or (R)-4-benzyloxazolidinone with a mixed anhydride of a methoxyphenylacetic acid under conditions which forms a (4S or 4R)-4-benzyl-3-[(methoxyphenyl)acetyl]-1,3-oxazolidin-2-one having the structure:

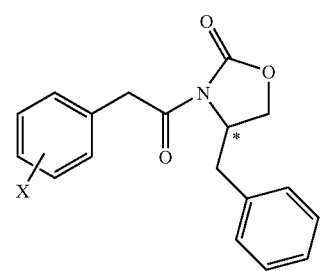

wherein X is methoxy or trifluoromethoxy;

(b) treating the (4S)- or (4R)-4-benzyl-3-[(methoxyphenyl)acetyl]-1,3-oxazolidin-2-one with an aprotic amine base and titanium chloride in a chlorinated solvent under conditions which permit formation of the corresponding anion;

(c) mixing the corresponding anion with titanium chloride and cyclohexanone under conditions which permit an aldol reaction to form the corresponding (4S)- or (4R)-4-benzyl-3-[(2R or 2S)-2-(1-hydroxycyclohexyl)-2-(methoxyphenyl)acetyl]-1,3-oxazolidin-2-one having the structure shown below:

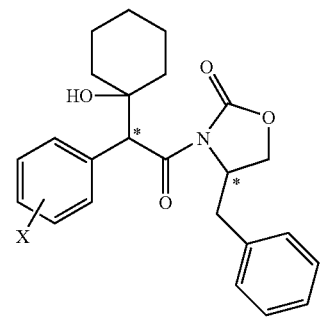

wherein X is OCH$_3$ or OCF$_3$;

(d) hydrolyzing the (4S)- or (4R)-4-benzyl-3-[(2R or 2S)-2-(1-hydroxycyclohexyl)-2-(methoxyphenyl)acetyl]-1, 3-oxazolidin-2-one to form chiral (2R or 2S)-(1-hydroxycyclohexyl)-methoxyphenyl)acetic acid having the structure shown below:

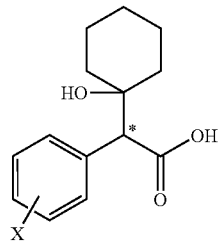

wherein X is $OCH_3$ or $OCF_3$;

(e) coupling the chiral acetic acid with a secondary amine $NR_1R_2$ to form an amide having the structure shown below:

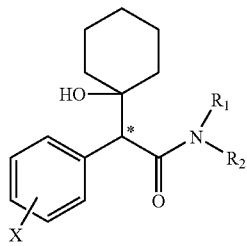

wherein X is $OCH_3$ or $OCF_3$, $R_1$ and $R_2$ are each independently selected from $C_1$-$C_3$ alkyl, or together with the nitrogen they are attached form a 1,4-piperazine ring wherein said piperazine ring is substituted with from 0 to 2 methyl groups; and (f) reducing the amide to form an (S)- or (R)-1-[(2-amino)-1-(methoxyphenyl)ethyl]cyclohexanol (compound of formula I) or pharmaceutically acceptable salt thereof.

In still a further aspect, the invention provides a (2R)-(1-hydroxycyclohexyl)(methoxyphenyl)acetic acid. In one embodiment, the compound may be selected from (2R)-2-(1-hydroxycyclohexyl)-2-(4-methoxyphenyl)acetic acid and (2R)-2-(1-hydroxycyclohexyl)-2-(3-trifluoromethoxyphenyl)acetic acid.

In yet a further aspect, the invention provides a compound (2R)-2-(1-hydroxycyclohexyl)-2-(methoxyphenyl)-$NR_1R_2$ dimethylacetamide. In one embodiment, the compound may be selected from (2R)-2-(1-hydroxycyclohexyl)-2-(4-methoxyphenyl)-N,N-dimethylacetamide and 1-(3,5-Dimethylpiperazin-1-yl)-2-(R)-(1-hydroxy-cyclohexyl)-2-(3-trifluoromethoxyphenyl)-ethanone.

The invention also provides an enantioselective process for the production of a specific enantiomer of venlafaxine or a salt or derivative thereof.

Other aspects and advantages of this application will be readily apparent from the following detailed description of the invention.

DETAILED DESCRIPTION OF THE INVENTION

In one aspect, the invention provides a method for enantiomer-specific synthesis of venlafaxine comprising the steps described herein.

Advantageously, the present invention, by permitting the selection of the R or S enantiomer of venlafaxine, permits one to adjust the ratio of norepinephrine reuptake inhibition/serotonin inhibition of the venlafaxine. For example, the R enantiomer of venlafaxine is approximately 10 times more selective for the serotonin transporter as compared to the norepinephrine transporter. The S enantiomer of venlafaxine on the other hand is approximately 75 times more selective for the serotonin transporter as compared to the norepinephrine transporter, whilst the racemate of venlafaxine is about 20 times more selective for the serotonin transporter as compared to the norepinephrine transporter. A variety of uses for selective serotonin/norepinephrine reuptake inhibitors are well known to those of skill in the art.

According to the present invention, "enantiomer-specific" or "essentially a single enantiomer" refers to a reaction which preferentially yields 90% to 100% of an (S) enantiomer or 90% to 100% of an (R) enantiomer of the compound. For example, a reaction of the invention may yield at least 95%, at least 97%, or at least 99% of an (R)-enantiomer of the compound, which has less than 5%, less than 3%, or less than 1% (S)-enantiomer. In another example, a reaction of the invention yields at least 95%, at least 97%, or at least 99% of an (S)-enantiomer of the compound, which has less than 5%, less than 3%, or less than 1% (R)-enantiomer.

The method of the invention yields optically pure venlafaxine, i.e., (S)- or (R)-, venlafaxine. Further, the reaction can be used to generate optically pure, desmethylvenlafaxine. This compound can be generated by demethylating the venlafaxine prepared according to the present invention, using described methods. However, other, optically pure 2-phenyl-2-(1-hydroxycycloalkyl)ethylamines can be synthesized using the method of the invention. Thus, (S)-2-phenyl-2-(1-hydroxycycloalkyl)ethylamines, or (R)-2-phenyl-2-(1-hydroxycycloalkyl)ethylamines and mixtures thereof, can be synthesized utilizing the method of the invention, with optional additional steps utilized to generate a selected derivative according to known techniques.

The term "optically pure" refers to e.g. venlafaxine or other 2-phenyl-2-(1-hydroxycycloalkyl)ethylamines as defined herein which is a (R)-venlafaxine or other (R)-2-phenyl-2-(1-hydroxycycloalkyl)ethylamines substantially free of their (S)-stereoisomer, or (S)-venlafaxine or other (S)-2-phenyl-2-(1-hydroxycycloalkyl)ethylamines substantially free of their (R)-stereoisomers.

As used herein "substantially free" means that the compositions contains at least 90%, at least 95%, at least 97%, or at least 99%, or 100%, by weight of a (R)- or (S)-venlafaxine having a single optical rotation and 10%, 3%, 1%, or less, by weight of a venlafaxine having the opposing rotation. These percentages are based upon the total amount of venlafaxine in the composition. The terms "substantially optically pure (R)-isomer of venlafaxine" or "substantially optically pure (S)-venlafaxine" and "optically pure (R)-isomer of venlafaxine" and "optically pure (S)-venlafaxine" are also encompassed by the above-described amounts.

The optically pure compounds of the invention further encompass compounds which can be essentially single diastereomers The term "essentially a single diastereomer" refers to compounds which are substantially free of another diastereomer, i.e, within the ranges provided in the preceding paragraph.

As used herein, the term venlafaxine refers to 1-[2-dimethylamino)-1-(4-methoxyphenyl)ethyl]cyclohexanol or salts thereof. For example encompassed by this term are the hydrochloride salt of 1-[2-dimethylamino)-1-(4-methoxyphenyl)ethyl]cyclohexanol and other salts derived from pharmaceutically acceptable acids. This invention also contemplates additional 2-phenyl-2-(1-hydroxycycloalkyl)ethylamines and pharmaceutically acceptable salts thereof wherein various methoxy or trifluoromethoxy isomers are prepared or wherein amines other than dimethylamine are present. In some embodiments of this invention, processes of this invention are useful for the preparation of compounds of formula I as shown below:

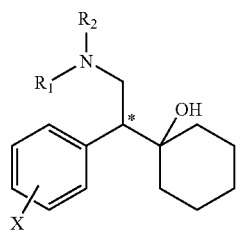

I

Wherein X is $OCH_3$ or $CF_3$, $R_1$ and $R_2$ are each independently selected from $C_1$-$C_3$ alkyl, or together with the nitrogen they are attached form a 1, 4-piperazine ring wherein said piperazine ring is substituted with from 0 to 2 methyl groups.

Specific examples of 2-phenyl-2-(1-hydroxycycloalkyl) ethylamines that maybe advantageously prepared by the processes described herein are 1-{(1S)-2-[cis-3,5-dimethylpiperazine-1-yl]-1-[3-(trifluoromethoxy)phenyl]ethyl}cyclohexanol, which is described in US Published Patent Application No. 2005-0143579, O-desmethylvenlafaxine [US Published Patent Appln No. 20030105358], and the succinate salt of O-desmethylvenlafaxine as described in US Published Patent Appln No. 20050096479; US Published Patent Appln No. 20040190952; U.S. patent application Ser. No. 11/486,324 (filed internationally as PCT/US06/27106); U.S. patent application Ser. No. 11/485,693; U.S. patent application Ser. No. 11/486,336; and U.S. patent application Ser. No. 11/485,663 (filed internationally as PCT/US06/26991).

For purposes of this invention, the term "methoxyphenyl" when used as part of a named structure, but where the location of the methoxy group is not indicated, refers to a generic structure where the phenyl ring is substituted with a methoxy or trifluoromethoxy group at any position of the phenyl ring. Also for purposes of this invention, the term "amino" when used as part of a named structure but where the amino group is not further defined, refers generically to a compound where the amino group is a tertiary amine. By way of non-limiting examples, "amino" where not already defined can be dimethylamino or cis-3,5-dimethylpiperazine-1-yl.

Salts of venlafaxine and derivatives thereof include, but are not limited to, the following salts with organic and inorganic acids such as acetic, lactic, citric, tartaric, succinic, fumaric, maleic, malonic, mandelic, mallic, hydrochloric, hydrobromic, phosphoric, nitric, sulfuric, methanesulfonic, toluenesulfonic and similarly known acceptable acids, and mixtures thereof. Other salts include salts with alkali metals or alkaline earth metals, such as sodium (e.g., sodium hydroxide), potassium (e.g., potassium hydroxide), calcium or magnesium.

These salts, as well as other compounds described herein may be in the form of esters, carbamates and other conventional "pro-drug" forms, which, when administered in such form, convert to the active moiety in vivo. In a currently preferred embodiment, the prodrugs are esters. See, e.g., B. Testa and J. Caldwell, "Prodrugs Revisited: The "Ad Hoc" Approach as a Complement to Ligand Design", Medicinal Research Reviews, 16(3):233-241, ed., John Wiley & Sons (1996).

Synthesis

In one embodiment, a (4S)-4-benzyl-3-[(methoxyphenyl) acetyl]-1,3-oxazolidin-2-one, is treated with a base, in some cases with an aprotic amine base, and a Lewis acid, in some cases titanium chloride in a solvent, e.g. a chlorinated solvent, under conditions which allow the corresponding anion to form. The anion is then optionally mixed with a Lewis acid, in some cases titanium chloride, and cyclohexanone to form a (4S)-4-benzyl-3-[(2R)-2-(1-hydroxycyclohexyl)-2-(methoxyphenyl)acetyl]-1,3-oxazolidin-2-one.

This compound may be used for a variety of purposes, including to synthesize a compound of formula I (e.g., (S)-venlafaxine) via, for example, the hydrolysis of the oxazolidinone, formation of a tertiary amide and reduction to the desired tertiary amine. Alternatively, (4R)-4-benzyl-3-[(methoxyphenyl)acetyl]-1,3-oxazolidin-2-one maybe used to prepare the optical antipode (e.g. (R)-venlafaxine).

The reagents used in this invention can be either commercially obtained or can be prepared by standard procedures described in the literature. The compounds used in the present invention can be prepared using the methods described below, together with synthetic methods known in the synthetic organic arts or variations of these methods by one skilled in the art. [See, generally, *Comprehensive Organic Synthesis*, "Selectivity, Strategy & Efficiency in Modern Organic Chemistry", ed., I. Fleming, Pergamon Press, New York (1991); *Comprehensive Organic Chemistry*, "The Synthesis and Reactions of Organic Compounds", ed. J. F. Stoddard, Pergamon Press, New York (1979)]. Suitable methods include, but are not limited to, those outlined below.

In accordance with this invention, S-1-[2-(dimethylamino)-1-(4-methoxyphenyl)ethyl]cyclohexanol hydrochloride ((S)-venlafaxine hydrochloride) can be produced by the following reaction scheme (Scheme 1). Alternatively, if it is desired to make R-1-[2-(dimethylamino)-1-(4-methoxyphenyl)ethyl]cyclohexanol hydrochloride (R(−)-venlafaxine hydrochloride), this can be accomplished using the chemistry in Scheme 1 but by replacing (S)-4-benzyloxazolidinone with (R)-4-benzyloxazolidinone.

Similarly, other 2-phenyl-2-(1-hydroxycycloalkyl)ethylamines including salts can be generated using the method of the invention with the appropriate acids substituted for 4-methoxyphenyl acetic acid (compound I) and/or HCl in the reduction step.

In another embodiment, a single enantiomer of a 2-phenyl-2-(1-hydroxycycloalkyl)ethylamines is generated according to the method of the invention in which the appropriate starting materials are substituted for the amine and phenylacetic acid in the scheme. For example, in one embodiment, as also shown in Scheme 1, the amine is 2,6-(cis)-dimethylpiperazine (rather than dimethylamine) and the starting material is 3-(trifluoromethoxy)phenylacetic acid instead of 4-methoxyphenylacetic acid. The resulting 2-phenyl-2-(1-hydroxycloalkyl)ethylamine is 1-{(1S)-2-[cis-3,5-dimethylpiperazine-1-yl]-1-[3-(trifluoromethoxy)phenyl]ethyl}-cyclohexanol, which is a potent norepinephrine reuptake inhibitor. If desired, of course, its optical antipode may be prepared using the same method In another embodiment, a single enantiomer of a 2-phenyl-2-(1-hydroxycycloalkyl)ethylamine is produced by one or more modifications made to an enantiomer of a 2-phenyl-2-(1-hydroxycycloalkyl)ethylamine is produced according to the method of the invention. For example, in order to generate O-desmethylvenlafaxine, an additional step may be added following the final reduction step, i.e., to remove the methyl of the methoxyphenyl group. This may be accomplished by any conventional method for converting an aromatic methoxy group to a phenol. Suitable reagents may include Lewis acids. For example, boron tribromide may be utilized in combination with cyclohexene as a scavenger for HBr, or boron trichloride in combination with tetrabutylammonium iodide [PR Brooks et al, *J Org Chem*, 1999, 64:97619].

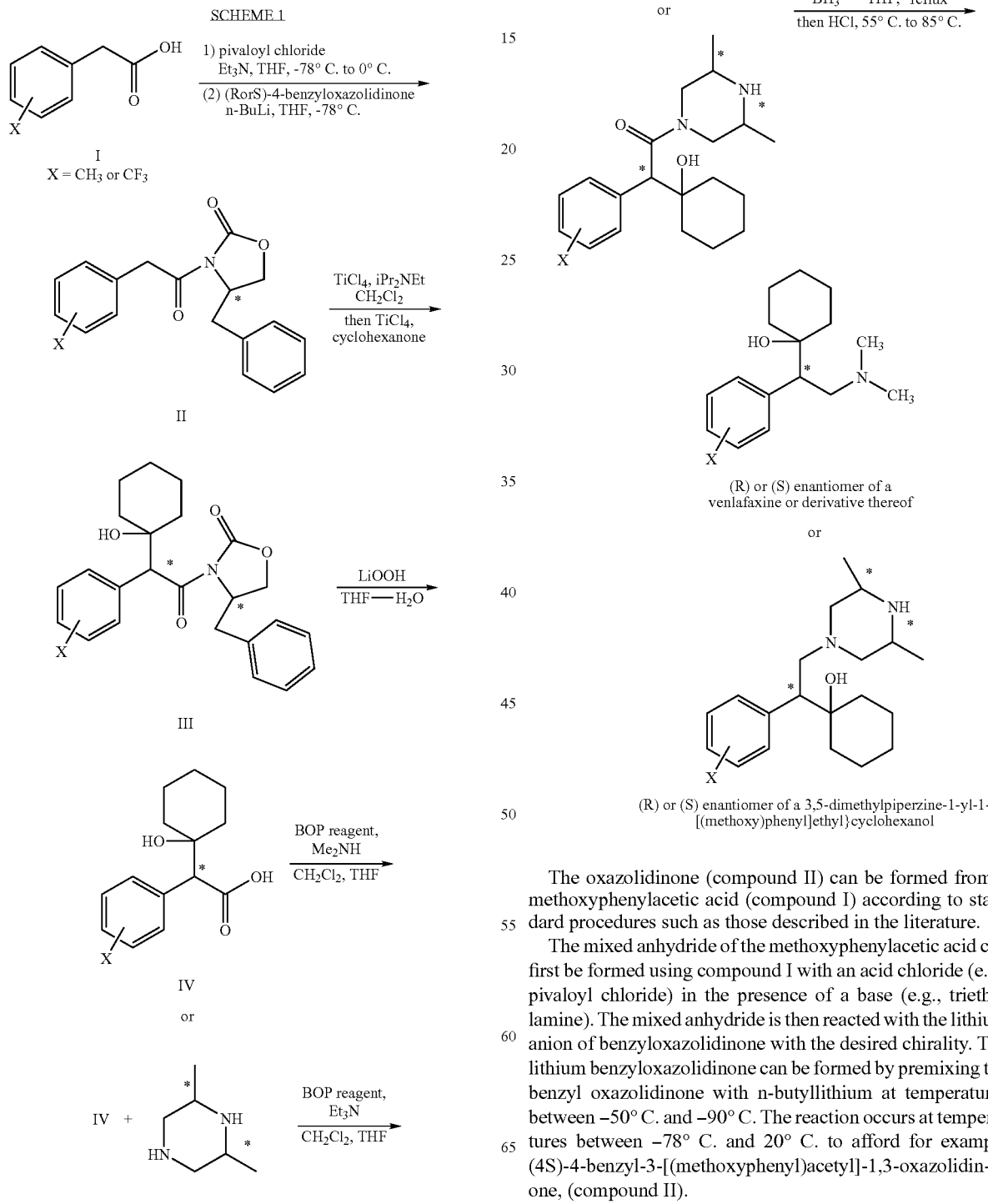

(R) or (S) enantiomer of a venlafaxine or derivative thereof or (R) or (S) enantiomer of a 3,5-dimethylpiperzine-1-yl-1-[(methoxy)phenyl]ethyl}cyclohexanol The oxazolidinone (compound II) can be formed from a methoxyphenylacetic acid (compound I) according to standard procedures such as those described in the literature.

The mixed anhydride of the methoxyphenylacetic acid can first be formed using compound I with an acid chloride (e.g., pivaloyl chloride) in the presence of a base (e.g., triethylamine). The mixed anhydride is then reacted with the lithium anion of benzyloxazolidinone with the desired chirality. The lithium benzyloxazolidinone can be formed by premixing the benzyl oxazolidinone with n-butyllithium at temperatures between −50° C. and −90° C. The reaction occurs at temperatures between −78° C. and 20° C. to afford for example (4S)-4-benzyl-3-[(methoxyphenyl)acetyl]-1,3-oxazolidin-2-one, (compound II).

As illustrated in Scheme 1, in one embodiment of the invention, (4S or 4R)-4-benzyl-3-[(4-methoxyphenyl)acetyl]-1,3-oxazolidin-2-one (compound II) is formed from the mixed anhydride of 4-methoxyphenylacetic acid (formed with an acid chloride, preferably pivaloyl chloride in the presence of a base, e.g., triethylamine or sodium hydride, at temperatures between −78° C. and 20° C.) and is reacted with the lithium anion of benzyloxazolidinone with the desired chirality. In another embodiment of the invention, (4S or 4R)-4-benzyl-3-{[3-(trifluoromethoxy)phenyl]acetyl}-1,3-oxazolidon-2-one is formed from the mixed anhydride of 3-trifluoromethoxyphenylacetic acid using the procedure described above. In one embodiment, the triethylamine-mediated mixed anhydride procedure is desirable.

Compound II is treated with an aprotic amine base, e.g., diisopropylethylamine, and titanium (IV) chloride in a chlorinated solvent, e.g., methylene chloride, at temperatures between −50° C. and −90° C. The anion is then allowed to form at temperatures between −20° C. and 20° C. After formation, the anion is re-cooled to between −50° C. and −90° C., an additional equivalent of titanium (IV) chloride followed by cyclohexanone is added, and the reaction is warmed to between −20° C. and 20° C. where the aldol reaction occurs.

According to the method of the invention, the chiral center in the enantiomerically-specific venlafaxine synthesis, is formed via the titanium-mediated aldol reaction [Takacs, et al., J Org Chem, 1998, 63, 2742-2748] of (4S)-4-benzyl-3-[(methoxyphenyl)acetyl]-1,3-oxazolidin-2-one (compound II) with cyclohexanone to form the intermediate oxazolidinone, (4S)-4-benzyl-3-[(2R)-2-(1-hydroxycyclohexyl)-2-(methoxyphenyl)acetyl]-1,3-oxazolidin-2-one (compound III). Suitably, this reaction can be stopped with a suitable quenching reagent, e.g., aqueous sodium bicarbonate, aqueous potassium phosphate, ammonium chloride, or the like. Typically, the final pH of the aqueous phase is more than about 3, or in the range of about 2 to about 6. Other suitable reaction conditions will be readily apparent to one of skill in the art.

In one desirable embodiment, and in contrast to the aldol reactions described in the literature, shorter reaction times have been found to provide a better ratio of starting material to product in the reactions of the invention (e.g., 17:83 as compared to 35:65 with the longer reaction times). Thus, while reaction times of 60 minutes or more have been described as desirable or necessary in the literature, shorter reaction times (e.g., 15 to 25 minutes, or 15 to 20 minutes, or 18 minutes), provide a desirable ratio of product to starting material.

The chiral acid, e.g. (2R)-(1-hydroxycyclohexyl)(methoxyphenyl)acetic acid (compound IV), is synthesized from (4S)-4-benzyl-3-[(2R)-2-(1-hydroxycyclohexyl)-2-(methoxyphenyl)acetyl]-1,3-oxazolidin-2-one (compound III) via hydrolysis of the oxazolidinone. According to one embodiment of this invention, a [1-hydroxycyclohexyl)(methoxy)phenyl]acetic acid is synthesized by lithium hydroperoxide hydrolysis of the chiral 4-benzyl-2-oxazolidinone. The lithium hydroperoxide may be formed by premixing lithium hydroxide and hydrogen peroxide. In one embodiment, 2 equivalents of the lithium hydroxide monohydrate are used. Suitably, improvements in yield and impurity profile might be realized with the slow addition of one equivalent of lithium hydroxide monohydrate to a solution of the oxazolidinone and hydrogen peroxide in THF. This both minimizes the retro-aldol pathway and improves the ratio of by-product to product.

However, other conventional methods for the hydrolysis of an oxazolidinone that do not cause racemization may be utilized for this conversion.

In accordance with one embodiment of this invention, S)-1-[2-(dimethylamino)-1-(methoxyphenyl)ethyl]cyclohexanol (S venlafaxine) is synthesized from the chiral acid, (2R)-(1-hydroxycyclohexyl)(methoxyphenyl)acetic acid (compound IV) via a coupling reaction followed by an amide reduction.

Any conventional means for coupling a chiral phenylacetic acid to a secondary amine can be utilized for this conversion; likewise, any conventional method for reducing an amide to form an amine can be utilized for this conversion.

In accordance with an embodiment of this invention, (2R)-(1-hydroxycyclohexyl)(4-methoxyphenyl)acetic acid (compound IV) is coupled with dimethylamine using benzotriazol-1-yl-oxy-tris(dimethylamino)phosphonium hexafluorophosphate in the presence of a base in a chlorinated solvent, e.g., methylene chloride. In one embodiment, excess dimethylamine, excess triethylamine, or trimethylamine, (e.g., about 10 eq.), is added to drive the reaction to completion. The material may be purified by chromatography or other suitable means. This coupling reaction may also be performed by a reaction of the amine with the acid chloride of (2R)-(1-hydroxycyclohexyl)(4-methoxyphenyl)acetic acid (compound IV) as is reported in the literature. [Yardley, John P.; Husbands, G. E. Morris; Stack, Gary; Butch, Jacqueline; Bicksler, James; Moyer, John A.; Muth, Eric A.; Andree, Terrance; Fletcher, Horace, III, et. al., *J. Med. Chem.* 1990, 33(10), 2899-905].

In one embodiment, the amide (V) is reduced using borane-tetrahydrofuran complex at temperatures between 55° C. to 85° C. in tetrahydrofuran. The resulting borane complex can be dissociated with either dilute acid, e.g., 2 N hydrochloric acid, or methanol. The material may be purified by crystallization from a mixed solvent of ethanol and diethylether as the dihydrochloride salt, which is then triturated twice with hot ethanol. Other purification procedures will be apparent to one of skill in the art.

The invention provides a method of generating enantiomerically pure compounds, thus providing compounds with a different ratio of serotonin reuptake inhibition to norepinephrine reuptake inhibition than the currently available dual serotonin and norepinephrine reuptake inhibitors (SNRIs). This attribute is very attractive for indications like irritable bowel syndrome (IBS) where the higher NE activity of SNRI's limits their application because of constipation side effects. This lower NE activity is also attractive for patients that have cardiovascular risks related to the side effect of hypertension. It also has an application in dealing with urinary incontinence. The compositions of the present invention can be used to treat or prevent central nervous system disorders including, but not limited to, depression (including but not limited to, major depressive disorder, bipolar disorder and dysthymia), fibromyalgia, anxiety, panic disorder, agorophobia, post traumatic stress disorder, premenstrual dysphoric disorder (also known as premenstrual syndrome), attention deficit disorder (with and without hyperactivity), obsessive compulsive disorder (including trichotillomania), social anxiety disorder, generalized anxiety disorder, autism, schizophrenia, obesity, anorexia nervosa, bulimia nervosa, Gilles de la Tourette Syndrome, vasomotor flushing, cocaine and alcohol addiction, sexual dysfunction, (including premature ejaculation), borderline personality disorder, chronic fatigue syndrome, incontinence (including fecal incontinence, overflow incontinence, passive incontinence, reflex incontinence, stress urinary incontinence, urge incontinence, urinary exertional incontinence and urinary incontinence), pain (including but not limited to migraine, chronic back pain, phantom limb pain, central pain, neuropathic pain such as diabetic neuropathy, and postherpetic neuropathy), Shy Drager syndrome, Raynaud's syndrome, Parkinson's Disease, epilepsy, and others. Compounds and compositions of the present invention can also be used for preventing relapse or recurrence of depression; to treat cognitive impairment; for the inducement of cognitive enhancement in patient suffering from senile dementia, Alzheimer's disease, memory loss, amnesia and amnesia syndrome; and in regimens for cessation of smoking or other tobacco uses. Additionally, compounds and compositions of the present invention can be used for treating hypothalamic amenorrhea in depressed and non-depressed human females.

The following examples are provided to illustrate the invention and do not limit the scope thereof. One skilled in the art will appreciate that although specific reagents and conditions are outlined in the following examples, modifications can be made which are meant to be encompassed by the spirit and scope of the invention.

EXAMPLE 1

Synthesis of (S)-1-[2-(Dimethylamino)-1-(4-methoxyphenyl)ethyl]cyclohexanol hydrochloride

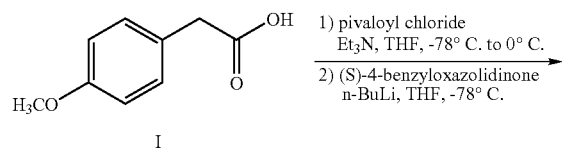

I

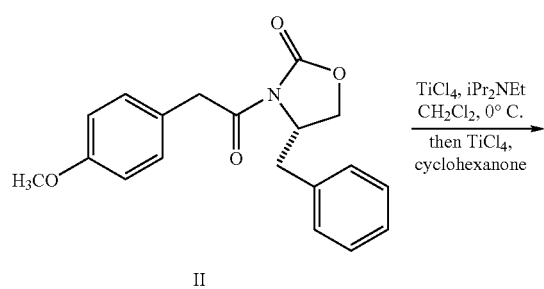

II

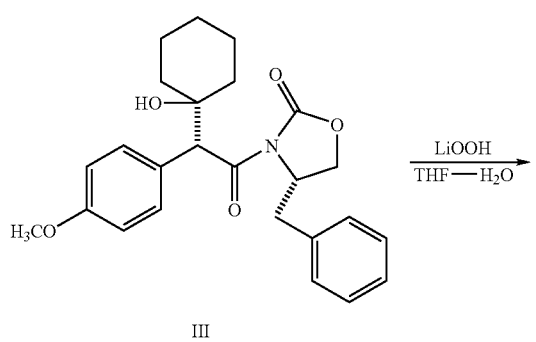

III

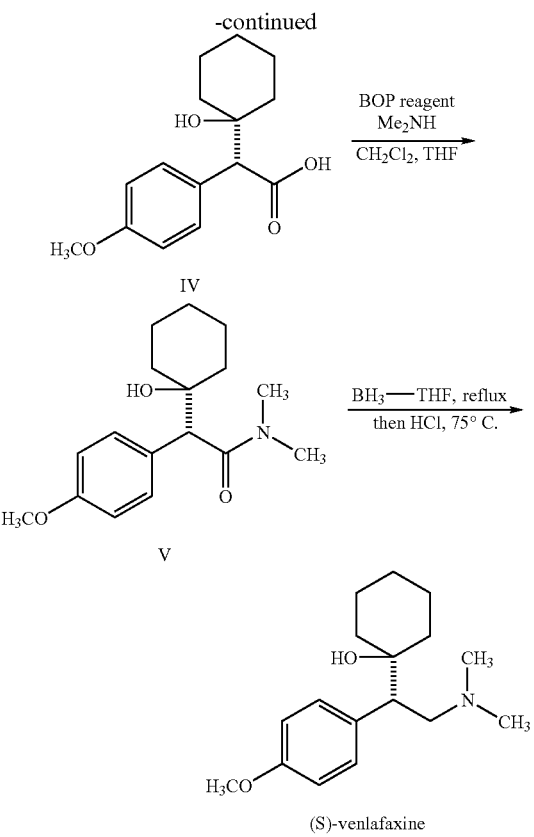

(S)-venlafaxine

A solution of 4-methoxyphenylacetic acid (1.0 g, 6.02 mmol) in dry tetrahydrofuran (15 mL) under nitrogen was cooled to −78° C. and treated dropwise with triethylamine (1.01 mL, 7.23 mmol) followed by pivaloyl chloride (0.78 mL, 6.32 mmol). The resulting solution was stirred at −78° C. for 15 min, and was then allowed to warm to 0° C. where it was stirred for 1.5 hours to form the mixed anhydride. Meanwhile, in a separate flask, a solution of (S)-4-benzyloxazolidinone (2.13 g, 12.04 mmol) in dry tetrahydrofuran, under nitrogen, was cooled to −78° C. and was treated dropwise with n-butyllithium (2.35 M solution in hexanes, 4.86 mL, 12.16 mmol). This solution was stirred at −78° C. for 15 min before it was transferred, via cannula, into the mixture containing the mixed anhydride that had been re-cooled to −78° C. After addition, the reaction mixture was stirred at −78° C. for 15 minutes before allowing it to warm to room temperature where it was stirred for 12 hours. The reaction was then quenched by the addition of a saturated aqueous solution of sodium bicarbonate, and the tetrahydrofuran was removed in vacuo. The resulting residue was partitioned between water (20 mL) and ethyl acetate (30 mL) and the layers were separated. The aqueous layer was extracted with ethyl acetate (3×30 mL) and the combined organic extracts were dried over magnesium sulfate and concentrated. The resulting residue was purified via Biotage™ Horizon chromatography (FLASH 40 M, silica, gradient from 5% ethyl acetate/hexane to 40% ethyl acetate/hexane) to yield 1.88 g (96%) (4S)-4-benzyl-3-[2-(4-methoxyphenyl)acetyl]-1,3-oxazolidin-2-one as a pale yellow solid. MS (ESI) m/z 326; $[\alpha]_D^{25}=+193°$ (c=0.010 g/mL, EtOH).

A solution of (4S)-4-benzyl-3-[2-(4-methoxyphenyl) acetyl]-1,3-oxazolidin-2-one (2.5 g, 7.68 mmol) in dry methylene chloride (50 mL) was cooled to −78° C. and treated with diisopropylethylamine (1.09 g, 8.45 mmol) followed by titanium tetrachloride (0.88 mL, 8.06 mmol). The resulting reaction was warmed to 0° C. where it was stirred for 1 h, during which time the reaction turned dark purple. The reaction was then re-cooled to −78° C. and was treated with another portion of titanium tetrachloride (0.88 mL, 8.06 mmol) followed by a solution of cyclohexanone (0.91 mL, 8.83 mmol) in methylene chloride (10 mL). After addition, the reaction was warmed to 0° C. where it was stirred for 2 h, after which time the reaction was carefully quenched with the addition of a saturated aqueous solution of sodium bicarbonate and the mixture was stirred at 0° C. for 30 minutes. The reaction was filtered to remove the titanium salt that had precipitated, and the layers of the filtrate were then separated. The aqueous layer was washed with methylene chloride (3×30 mL). The solid precipitate was then collected and stirred vigorously in a 2N aqueous solution of hydrochloric acid (50 mL) for 20 minutes, after which time, the remaining product was extracted from the aqueous layer with methylene chloride (3×60 mL), and the combined organic extracts (from the filtrate and the liberated salt) were dried over magnesium sulfate and concentrated in vacuo. The product was purified via Biotage™ Horizon chromatography (FLASH 40 M, silica, gradient from 10% ethyl acetate/hexane to 45% ethyl acetate/hexane) to yield 2.67 g (82%) (4S)-4-benzyl-3-[(2R)-2-(1-hydroxycyclohexyl)-2-(4-methoxyphenyl)acetyl]-1,3-oxazolidin-2-one as a colorless foam. MS (ESI) m/z 406; $[\alpha]_D^{25}$=+109° (c=0.010 g/mL, EtOH).

A solution of (4S)-4-benzyl-3-[(2R)-2-(1-hydroxycyclohexyl)-2-(4-methoxyphenyl)-acetyl]-1,3-oxazolidin-2-one (1.02 g, 2.4 mmol) in 4:1 tetrahydrofuran/water (25 mL) at 0° C. was treated dropwise with a premixed solution of hydrogen peroxide (50% in water, 0.59 mL, 9.6 mmol) and lithium hydroxide monohydrate (115 mg, 4.8 mmol) in water (1 mL). The reaction was stirred at 25° C. for 2 h after which time the tetrahydrofuran was evaporated in vacuo and the aqueous layer was treated with a 2 N aqueous solution of sodium hydroxide (5 mL). The aqueous layer was extracted with ethyl acetate (2×15 mL) followed by methylene chloride (2×15 mL) and the aqueous layer was acidified to pH=2 with a 2 N aqueous solution of hydrochloric acid. The product was extracted with ethyl acetate (3×50 mL) and the combined organic extracts were dried over magnesium sulfate and concentrated to yield a white solid which was recrystallized from ethyl acetate/hexane to yield 565 mg (89%) (2R)-(1-hydroxycyclohexyl)-2-(4-methoxyphenyl)acetic acid. MS (ESI) m/z 247; MS (ESI) m/z 263; $[\alpha]_D^{25}$=+71° (c=0.010 g/mL, EtOH); HRMS: calcd for $C_{15}H_{20}OO_4^+NH_4^+$, 282.16998; found (ESI-FT/MS, $[M^+NH_4]^{1+}$), 282.1706; enantiomeric excess >99%. The enantiomeric purity was determined, compared to the racemate, under the following Supercritical Fluid Chromatography conditions using Analytical Supercritical Fluid Chromatography (Berger Instruments, Inc. Newark, Del. USA):

| Column: | Chiralpak AD-H; 5μ, 250 mm × 4.6 mm ID (Chiral Technologies, Inc, Exton, PA, USA) |
|---|---|
| Column temperature: | 35° C. |
| SFC Modifier: | 20% MeOH |
| Flow rate: | 2.0 mL/min |
| Outlet Pressure: | 100 bar |
| Detector: | UV at 220 nm |

A solution of (2R)-(1-hydroxycyclohexyl)-2-(4-methoxyphenyl)acetic acid (156 mg, 0.59 mmol) in methylene chloride (1 mL) was treated with benzotriazol-1-yl-oxy-tris(dimethylamino)phosphonium hexafluorophosphate (313 mg, 0.71 mmol) and dimethylamine (2.0 M in tetrahydrofuran, 1.5 mL, 2.95 mmol). The reaction was stirred at 25° C. for 1.5 h after which time the solvent was evaporated and the product was purified via Biotage™ Horizon chromatography (FLASH 25 M, silica, gradient from 5% ethyl acetate/hexane to 36% ethyl acetate/hexane over 650 mL) to yield 160 mg (93%) (2R)-2-(1-hydroxycyclohexyl)-2-(4-methoxyphenyl)-N,N-dimethylacetamide as a white solid. MS (ESI) m/z 292; $[\alpha]_D^{25}$=+81° (c=0.010 g/mL, EtOH).

A solution of (2R)-2-(1-hydroxycyclohexyl)-2-(4-methoxyphenyl)-N,N-dimethylacetamide (135 mg, 0.46 mmol) in dry tetrahydrofuran (1 mL) was treated with a solution of borane (1.0 M in tetrahydrofuran, 1.02 mL, 1.02 mmol). The reaction was heated at 75° C. for 1.5 h, and was cooled to 0° C. and treated dropwise with a 2N aqueous solution of hydrochloric acid. The reaction was then heated at 75° C for 20 minutes, the reaction was cooled, and the tetrahydrofuran was removed in vacuo. The resulting residue was diluted with water (3 mL) and was washed with ethyl acetate (6 mL). The aqueous layer was then basified to pH=10 with a 2N aqueous solution of sodium hydroxide, and the product was extracted with methylene chloride (3×15 mL). The combined organic extracts were dried over magnesium sulfate and concentrated in vacuo to yield (1S)-1-[2-dimethylamino-1-(4-methoxyphenyl)ethyl]cyclohexanol as a colorless oil. The oil was dissolved in methanol (0.5 mL) and was treated with a saturated methanolic solution of hydrochloric acid followed by enough diethyl ether to cause crystallization to yield 127 mg (88%) S-1-[2-(dimethylamino)-1-(4-methoxyphenyl)ethyl]cyclohexanol hydrochloride as a white solid. MS (ESI) m/z 278; $[\alpha]_D^{25}$=−1.0° (c=0.010 g/mL, EtOH) (Yardley, John P.; Husbands, G. E. Morris; Stack, Gary; Butch, Jacqueline; Bicksler, James; Moyer, John A.; Muth, Eric A.; Andree, Terrance; Fletcher, Horace, III, et. al. *J. Med. Chem.* 1990, 33(10), 2899-905( $[\alpha]_D^{25}$=−4°, c=0.095 g/mL, EtOH); enantiomeric excess >99%. The enantiomeric purity was determined, compared to the racemate, under the following Supercritical Fluid Chromatography conditions using Analytical Supercritical Fluid Chromatography (Berger Instruments, Inc. Newark, Del. USA):

| Column: | Chiralpak AD-H; 5μ, 250 mm × 4.6 mm ID (Chiral Technologies, Inc, Exton, PA, USA) |
|---|---|
| Column temperature: | 35° C. |
| SFC Modifier: | 100% EtOH w/ 0.1% DEA |
| Flow rate: | 2.0 mL/min |
| Outlet Pressure: | 100 bar |
| Detector: | UV at 220 nm |

EXAMPLE 2

Synthesis of 1-[{(1S)-2-[cis-3,5-dimethylpiperazine-1-yl]-1-3-(trifluoromethoxy)phenyl]ethyl}-cyclohexanol This compound was prepared using essentially the same procedure as described in Example 1, using the appropriate starting materials substituted for the amine, i.e., 2,6-dimethylpiperazine rather than dimethylamine, and phenylacetic acid, i.e., 3-(trifluoromethoxy)phenylacetic acid instead of 4-methoxyphenylacetic acid. Other modifications to the procedure are as described in this example.

A. Synthesis of (4S)-4-benzyl-3-{([3-(trifluoromethoxy)phenyl]acetyl}-1,3-oxazolidin-2-one Two methods for the formation of (4S)-4-benzyl-3-{[3-(trifluoromethoxy)phenyl]acetyl}-1,3-oxazolidin-2-one were investigated.

Two 5 g reactions, using the optimized process conditions (1 equivalent each of all of the reagents) to prepare (4S)-4-benzyl-3-{[3-(trifluoromethoxy)phenyl]acetyl}-1,3-oxazolidin-2-one was investigated. Using the $Et_3N$-mediated mixed anhydride procedure afforded 5.75 g (analytically pure, 69.6%) of chromatographically isolated (4S)-4-benzyl-3-{[3-(trifluoromethoxy)phenyl]acetyl}-1,3-oxazolidin-2-one. Alternatively, the use of a NaH-mediated mixed anhydride in this procedure, afforded 5.16 g (analytically pure, 63.1%) of chromatographically isolated (4S)-4-benzyl-3-{[3-(trifluoromethoxy)phenyl]acetyl}-1,3-oxazolidin-2-one. The NaH-mediated mixed anhydride procedure generates hydrogen gas, whereas the $Et_3N$-mediated mixed anhydride procedure uses conditions that results in the precipitation of triethylammonium chloride creating a heterogeneous mixture that is apparently unreactive at −78° C. with the lithiated chiral auxiliary reagent.

The $Et_3N$-mediated mixed anhydride procedure gave a slightly higher and cleaner product (69.6% vs 63.1%) than a NaH-mediated mixed anhydride procedure.

B. Titanium-mediated Aldol Condensation (4S)-4-Benzyl-3-{(2R)-2-(1-hydroxycyclohexyl)-2-[3-(trifluoromethoxy)phenyl]acetyl}-1,3-oxazolidin-2-one was synthesized by a titanium-mediated aldol condensation. Shorter reaction times were used and, in contrast to literature references, were found to give a better ratio of starting material to product (17:83 vs 35:65). It was also important to use chromatographically pure starting material. In addition, this example illustrates quench in which the final pH was 6.0 instead of <3.0 or 8.5. A total of 36.8 g of (4S)-4-Benzyl-3-{(2R)-2-(1-hydroxycyclohexyl)-2-[3-(trifluoromethoxy)phenyl]acetyl}-1,3-oxazolidin-2-one was synthesized. The final material contained between 2.7% and 5.5% cyclohexanone, and was used without further purification in the subsequent step.

The following experiments describe some of the data supporting these conclusions.

Into a 2L 3-necked flask equipped with a mechanical stirrer, nitrogen inlet tube, and septum was placed (4S)-4-benzyl-3-[3-(trifluoromethoxy)phenyl]acetyl}-1,3-oxazolidin-2-one (19.56 g, 51.6 mmol) in methylene chloride (344 mL). The reaction was placed under nitrogen and cooled to −78° C. After 15 min, diisopropylethyl amine (9.89 mL, 56.8 mmol) was added, followed by titanium tetrachloride (5.94 mL, 54.18 mmol). Neat $TiCl_4$ was preferred over the 1 M solution in methylene chloride. After 5 min, the purple reaction mixture was stirred at 0° C. for 20 min.

The purple reaction mixture was re-cooled to −78° C. After 15 min titanium tetrachloride (5.94 mL, 54.18 mmol) was added, followed by cyclohexanone (6.4 mL, 61.9 mmol). Total addition time was 5 min. The purple reaction mixture was placed in an ice bath, and after 8 min the solution was less purple and more brown. After an additional 7 min (total time at 0° C. is 15 min) the reaction was poured into a stirred solution of ice (500 g), potassium phosphate monobasic (74 g), sodium bicarbonate (23 g), water (1 L), and ethyl acetate (800 mL). After vigorously stirring, the internal temperature was 5.7° C., and pH of aqueous was 6.0, which immediately dropped to 3.0. Additional sodium bicarbonate (20.8 g) was added to maintain a pH of 6.0; internal temperature is 6.4° C. The solution is poured into a separatory funnel and shaken vigorously. The cloudy aqueous layer is removed, and the cloudy ethyl acetate layer was washed with brine (300 mL), and then dried (sodium sulfate). The cloudy ethyl acetate layer, was passed through a Celite™ pad or a Whatman I filter paper, and the solvent was removed under reduced pressure. The 26 g of crude material was passed through a silica gel plug (1 kg) in a 2 L Buchner funnel with 10% ethyl acetate in hexanes (fractions 1-5, 1.8 L portions), then 20% ethyl acetate in hexanes (fractions 6, 1.8 L portion). Fractions 2-5 gave 15.58 g (63%) of an oil, which contained 2.7% of the cyclohexanone product. This material was used without further purification in the subsequent step.

C. Hydrolysis Reaction (2R)-(1-Hydroxycyclohexyl)[3-(trifluoromethoxy)phenyl]acetic acid was synthesized by lithium hydroperoxide hydrolysis of the chiral (S)-4-benzyl-2-oxazolidinone. A total of 14.9 g of (2R)-(1-Hydroxycyclohexyl)[3-(trifluoromethoxy)phenyl]acetic acid was synthesized from 25.5 g of (4S)-4-benzyl-3-{[3-(trifluoromethoxy)phenyl]acetyl}-1,3-oxazolidin-2-one.

The following experiments describe some of the data supporting these conclusions.

Into a 2 L 3-necked flask equipped with a magnetic stir bar, nitrogen inlet adapter, thermometer, and peristaltic pump inlet, was placed (4S)-4-benzyl-3-{(2R)-2-(1-hydroxycyclohexyl)-2-[3-(trifluoromethoxy)phenyl]acetyl}-1,3-oxazolidin-2-one, (13.56 g, 28.4 mmol) in THF (142 mL). The reaction was placed under nitrogen and cooled to 0° C. (ice/Dry Ice bath).

When the internal temperature reached 0.5° C., lithium hydroxide monohydrate (1.19 g, 28.4 mmol) and $H_2O_2$ in water (56.8 mL) was added at a rate of 0.3 mL/min. Addition was complete in 3 h. The reaction was stirred an additional 45 min (internal temp was 1° C). Aliquots were taken intermittently by diluting the reaction mixture (<0.1 mL) in $CH_3CN$ (1 mL) (see Table).

TABLE

HPLC peaks of reaction mixture aliquots

| Total Time | HPLC pk @ 1.823 min[a] (by-product) | 2.214 min (desired product) | 2.938 min (starting material) |
|---|---|---|---|
| 1 h | 1.5% | 28.4% | 70% |
| 3 h | 8.2 | 84 | 4.4 |
| 3 h 45' | 9.9 | 86.2 | 3.9 |

[a]Peaks visible at 230 nm; by-product was more visible at 230 nm than 254 nm

The cold reaction mixture was poured in portions into a stirred solution of sodium sulfite (63 g) in water (500 mL) and ice (200 g). The internal temperature increased from 1° C. to 26° C. Ice (200 g) was added to keep the temperature low. Final pH of the aqueous solution was 8.5. In one embodiment, the amount of hydrogen peroxide may be reduced from 10 equivalents to 4 equivalents to reduce the exothermic reaction.

The aqueous solution was extracted with methylene chloride (400 mL). The slightly opaque methylene chloride layer, which now contained the chiral auxiliary, was removed. The aqueous layer was poured into a beaker and acidified with solid citric acid monohydrate (59.7 g) to pH 3, then extracted with ethyl acetate (400 mL).

After drying the ethyl acetate layer over sodium sulfate, filtering, and removing the solvent under reduced pressure, gave 9.27 g of an oil. $^1$H NMR indicated the presence of desired product as well as citric acid, acetic acid, and ethyl acetate. The oil was taken up in methylene chloride (80 mL) and allowed to stand at room temperature as needles of citric acid crystallized out.

After 12 h, the methylene chloride solution was filtered, concentrated under reduced pressure, and left on a vacuum pump overnight to remove the residual ethyl acetate and acetic acid. This yielded 7.9 g (87.8%) of (2R)-(1-hydroxy-cyclohexyl)[3-(trifluoromethoxy)phenyl]acetic acid, which was combined with 7 g (87.5%) from another 12 g run.

D. Amination Reaction

In one experiment, (Benzotriazol-1-yloxy)tris(dimethylamino)phosphonium hexafluorophosphate (41.73 g, 94.35 mmol) and triethylamine (88 mL, 630 mmol) were added to a mixture of (R)-2-(1-hydroxycyclohexyl)-2-(3-(trifluoromethoxy)phenyl)acetic acid (20.0 g, 62.9 mmol) and cis-2,6-dimethylpiperazine (7.17 g, 62.9 mmol) in methylene chloride (150 mL) at RT. After stirring for 18 h, the mixture was concentrated in vacuo. The residue was purified by flash chromatography on silica gel (50 to 100% ethyl acetate in heptane) to afford 1-(3,5-Dimethyl-piperazin-1-yl)-2-(R)-(1-hydroxy-cyclohexyl)-2-(3-trifluoromethoxy-phenyl)-ethanone (24.3 g, 93%).

E. Reduction Reaction

To solution of 1-(3,5-Dimethyl-piperazin-1-yl)-2-(R)-(1-hydroxy-cyclohexyl)-2-(3-trifluoromethoxy-phenyl)-ethanone (24.7 g, 59.6 mmol) in THF (140 mL) was added BH$_3$.THF (300 mL, 1M, 300 mmol). The resultant mixture was heated to reflux for 22 h. On a smaller scale this reaction only takes about 2 h. After cooling down, 2N aqueous HCl (500 mL) was added to the mixture. After heating to reflux for 1 h, the mixture was allowed to cool down to RT and extracted with ethyl acetate (300 mL). The aqueous phase was basified with 50% NaOH to PH=12 and extracted with ethyl acetate (400 mL×4). The organic extracts were dried over Na$_2$SO$_4$ and concentrated in vacuo to provide crude 1-{(1S)-2-[cis-3,5-dimethylpiperazine-1-yl]-1-[3-(trifluoromethoxy)phenyl]ethyl}-cyclohexanol (14.6 g, 61%).

To crude 1-[{(1S)-2-[cis-3,5-dimethylpiperazine-1-yl]-1-[3-(trifluoromethoxy)phenyl]ethyl}-cyclohexanol (11.4 g) was added EtOH (200 proof, 140 mL). Some insoluble material was removed by filtration. To the resultant clear solution was added dropwise 2N HCl in ether (75 mL) at RT. Crystals formed slowly, which were collected by filtration and washed first with a mixture of EtOH & EtOAc, then with heptane to afford 1-{(1S)-2-[cis-3,5-dimethylpiperazine-1-yl]-1-[3-(trifluoromethoxy)phenyl]ethyl}-cyclohexanol (8.2 g, 95.23% purity by HPLC).

The above material was heated to reflux in EtOH (80 mL, 200 proof) for 1 h. Upon cooling down, the mixture was filtered to afford 1-{(1S)-2-[cis-3,5-dimethylpiperazine-1-yl]-1-[3-(trifluoromethoxy)phenyl]ethyl}-cyclohexanol with a purity of 97.43%. This material was heated to reflux in EtOH (80 mL, 200 proof) for 1 h one more time. Upon cooling down, the mixture was filtered to afford the product (6.9 g, 99.1% purity by HPLC, 100% chiral purity by HPLC).

All publications cited in this specification are incorporated herein by reference herein. While the invention has been described with reference to a particularly preferred embodiment, it will be appreciated that modifications can be made without departing from the spirit of the invention. Such modifications are intended to fall within the scope of the appended claims.

The invention claimed is:

1. A process for the stereoselective synthesis of a (4S or 4R)-4-benzy-3-[(2R or 2S)-(1-hydroxycyclohexyl)-(methoxyphenyl)acetyl]-1,3-oxazolidin-2-one having the structure

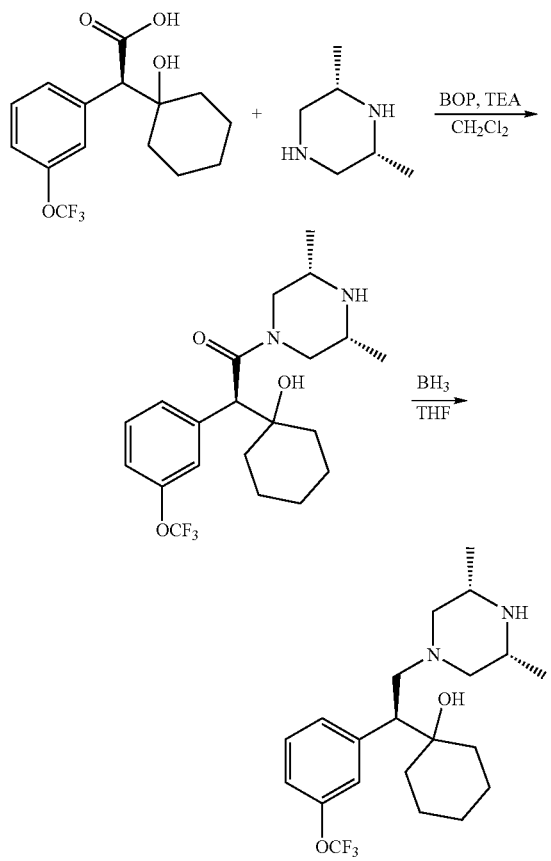

6.9 g
HPLC purity; 99.1%, LSI: 0.46%
Chiral HPLC purity: 100%

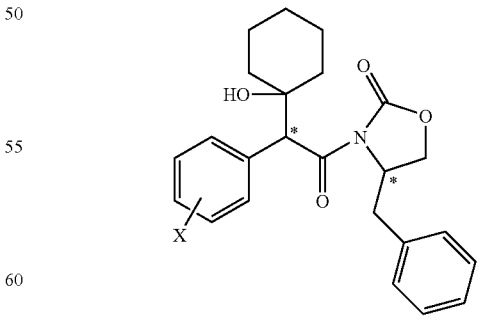

wherein X is methoxy or trifluoromethoxy;
comprising the steps of:
treating a (4S or 4R)-4-benzyl-3-[(methoxyphenyl)acetyl]-1,3-oxazolidin-2-one having the structure

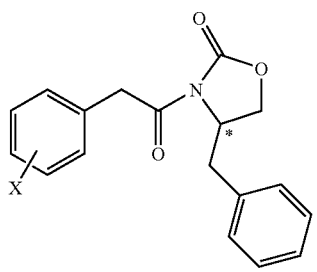

wherein X is methoxy or trifluoromethoxy;

with an aprotic amine base and titanium tetrachloride in a chlorinated solvent under conditions which permit formation of the corresponding anion; and mixing the corresponding anion with titanium tetrachloride and cyclohexanone under conditions which permit an aldol reaction to form said (4S or 4R)-4-benzyl-3-[(2R or 2S)-(1-hydroxycyclohexyl)-(methoxyphenyl)acetyl]-1,3-oxazolidin-2-one.

2. The process according to claim 1, wherein the (4S or 4R)-4-benzyl-3-[(methoxyphenyl)acetyl]-1,3-oxazolidin-2-one is a (4S or 4R)-4-benzyl-3-[(trifluoromethoxyphenyl)acetyl]-1,3-oxazolidin-2-one.

3. The process according to claim 1, wherein the aprotic amine base is diisopropyethylamine.

4. The process according to claim 1, wherein the chlorinated solvent is methylene chloride.

5. A compound having the structure:

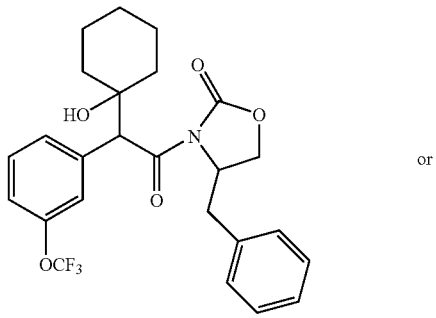

or

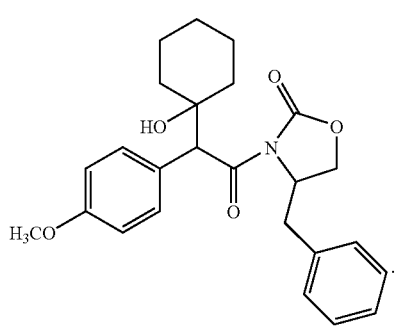

6. A process for the stereoselective synthesis of an enantiomer of a 2-phenyl-2-(1-hydroxycycloalkyl)ethylamine or salt thereof having the structure

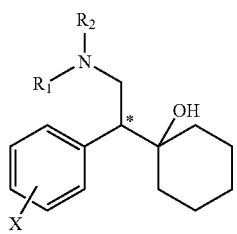

wherein X is OCH$_3$ or OCF$_3$, R$_1$ and R$_2$ are each independently selected from C$_1$-C$_3$ alkyl, or together with the nitrogen they are attached form a 1,4-piperazine ring wherein said piperazine ring is substituted with from 0 to 2 methyl groups said method comprising the steps of:

(a) reacting an (S)- or (R)-4-benzyl-1,3-oxazolidin-2-one with a mixed anhydride of a methoxyphenylacetic acid under conditions which form a (4S or 4R)-4-benzyl-3-[(methoxyphenyl)acetyl]-1,3-oxazolidin-2-one having the structure:

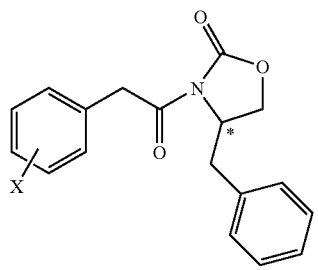

wherein X is OCH$_3$ or OCF$_3$;

(b) treating the (4S)- or (4R)-4-benzyl-3-[(methoxyphenyl)acetyl]-1,3-oxazolidin-2-one with an aprotic amine base and titanium tetrachloride in a chlorinated solvent under conditions which permit formation of the corresponding anion;

(c) mixing the corresponding anion with titanium tetrachloride and cyclohexanone under conditions which permit an aldol reaction to form the corresponding (4S)- or (4R)-4-benzyl-3-[(2R or 2S)-2-(1-hydroxycyclohexyl)-2-(methoxyphenyl)acetyl]-1,3-oxazolidin-2-one having the formula

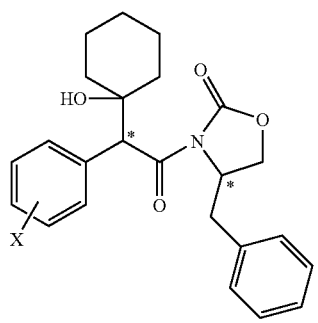

wherein X is OCH$_3$ or OCF$_3$;

(d) hydrolyzing the (4S)- or (4R)-4-benzyl-3-[(2R or 2S)-2-(1-hydroxycyclohexyl) -2-(methoxyphenyl)

acetyl]-1,3-oxazolidin-2-one to form chiral (2R or 2S)-(1-hydroxycyclohexyl) -methoxyphenyl)acetic acid having the formula

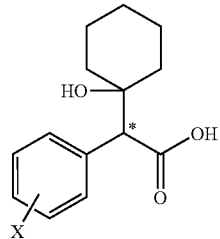

wherein X is OCH₃ or OCF₃;

(e) coupling the chiral phenylacetic acid with a secondary amine $NR_1R_2$ to form an amide having the formula

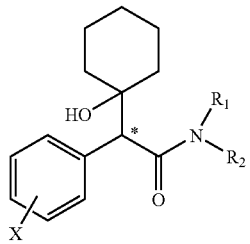

wherein X is OCH₃ or OCF₃, $R_1$ and $R_2$ are each independently selected from $C_1$-$C_3$ alkyl, or together with the nitrogen they are attached form a 1,4-piperazine ring wherein said piperazine ring is substituted with from 0 to 2 methyl groups;

(f) reducing the amide to form an (S)- or (R)-2-phenyl-2-(1-hydroxycycloalkyl)ethylamine;

(g) and optionally converting the free base to a salt thereof.

7. The process according to claim 6, wherein the reacting step (a) comprises reacting the mixed anhydride of a methoxyphenylacetic acid with a lithium anion of benzyl-1,3-oxazolidin-2-one at a temperature from −78° C. to 20° C.

8. The process of claim 6, wherein the base in step (b) is diisopropylethylamine.

9. The process of claim 6, wherein the chlorinated solvent of step (b) is methylene chloride.

10. The process according to claim 6, wherein the coupling step (e) comprises coupling the chiral phenylacetic acid with benzotriazol-1-yl-oxy-tris (dimethylamino)phosphonium hexafluorophosphate (BOP) in the presence of a base in a chlorinated solvent.

11. The process according to claim 6, wherein the reduction step (f) comprises reducing the amide formed by step (e) using a borane in tetrahydrofuran at temperatures of 55° C. to 85° C. to form a borane complex, and dissociating the borane complex to provide an enantiomer of 2-phenyl-2-(1-hydroxycycloalkyl)ethylamine.

12. The process according to claim 6, wherein X is 4-methoxy.

13. The process according to claim 6, wherein X is 3-trifluoromethoxy.

* * * * *